United States Patent [19]

Austin et al.

[11] Patent Number: 5,500,217
[45] Date of Patent: Mar. 19, 1996

[54] PERSONAL CARE FORMULATIONS

[75] Inventors: Peter W. Austin, Bury; Michael Singer, Cheadle Hulme, both of United Kingdom

[73] Assignee: Zeneca Limited, London, England

[21] Appl. No.: 98,315

[22] PCT Filed: Feb. 3, 1992

[86] PCT No.: PCT/GB92100191

§ 371 Date: Nov. 23, 1993

§ 102(e) Date: Nov. 23, 1993

[87] PCT Pub. No.: WO92/13520

PCT Pub. Date: Aug. 20, 1992

[30] Foreign Application Priority Data

Feb. 5, 1991 [GB] United Kingdom .................. 9102412
Feb. 3, 1992 [GB] United Kingdom .................. 9202235

[51] Int. Cl.$^6$ .......................... A61K 7/48; A61K 7/032; A61K 7/027; A61K 7/075
[52] U.S. Cl. ................ 424/401; 424/59; 424/64; 424/65; 424/70.1; 424/70.7; 424/73; 514/844; 514/845; 514/846; 514/847; 514/937; 514/938; 514/939; 514/944

[58] Field of Search ................... 424/401, 63, 64, 424/69, 70, 73, 59, 76.1; 514/844–847, 937–939, 944

[56] References Cited

U.S. PATENT DOCUMENTS 3,931,032 6/1976 Karsten .................................. 252/107

FOREIGN PATENT DOCUMENTS

| 249328 | 12/1987 | European Pat. Off. . |
| 0392648 | 10/1990 | European Pat. Off. . |
| 409617 | 1/1991 | European Pat. Off. . |
| 2446555 | 4/1975 | Germany . |

Primary Examiner—Jyothsna Venkat
Attorney, Agent, or Firm—Cushman Darby & Cushman

[57] ABSTRACT

A personal care formulation which contains, as an anti-microbial agent, a compound containing the structure —C(S)—N(OR)— or a salt or complex thereof, for example a 2:1 complex or salt of 3-hydroxy-4-methylthiazol-2(3H)thione and zinc. The personal care formulation may be an oil-in-water or water-in-oil emulsion such as hand lotions and emollient creams, or may be shampoos and the like. The anti-microbial agent has good activity against micro-organisms together with a low toxicity.

10 Claims, No Drawings

PERSONAL CARE FORMULATIONS

This application is a 371 of PCT/GB92/001 91 filed on Feb. 3, 1992.

The present invention relates to compositions which can be used in personal care applications and, in particular, to such compositions which contain an agent for protection against micro-organisms.

Compositions which may be used in personal care applications are of many types but are, in general, oil-in-water or water-in-oil emulsions. Many of these compositions are applied to the skin and may be, at least partially, absorbed by the skin. Such compositions include, inter alia, hand lotions, foundation creams, emollient creams, facial washing creams, shaving creams, after-shave lotions, sunscreen lotions and creams, sunscreen hair protectors, after sun lotions, antiperspirants, deodorants, hair gels, hair colourants and hair mousse. Other compositions which may be applied to the skin include various make-up formulations such as mascara, eye shadow, eyeliners, lipstick, lip gloss, facial blushes, rouges, foundations and fragrances. Most of the foregoing compositions are applied for long term contact with the skin. Other personal care products are used in a manner in which they make only temporary contact with the skin such as shampoos, shampoo gels, conditioning rinses, toothpaste, mouthwashes, foam bath liquids, miscible and soluble bath oils and liquid soap formulations. Many compositions which can be used in personal care applications are susceptible to the growth of micro-organisms and it is desirable to incorporate into these compositions a material which is effective to inhibit the growth of micro-organisms. However, many materials which possess anti-microbial activity either possess a satisfactory anti-microbial activity together with undesirable side effects or, if they have few or no side effects, show a low activity against micro-organisms.

We have now found that certain thiohydroxamic acid derivatives have useful anti-microbial activity and do not show appreciable undesirable side effects.

According to the present invention there is provided a personal care formulation which contains an anti-microbial agent wherein the anti-microbial agent is a compound of the general formula (I):

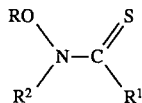

or a complex or salt thereof;
wherein:
R is hydrogen, a hydrocarbyl group, a substituted hydrocarbyl group, an acyl group, a substituted acyl group or a group —COOR³;

R¹ is a hydrocarbyl group or a substituted hydrocarbyl group;

R² is a hydrocarbyl group or a substituted hydrocarbyl group; or R¹ and R², together with the nitrogen and carbon atoms to which they are attached, form a heterocyclic ring; and R³ is a hydrocarbyl group.

It is preferred that when R¹ and R², together with the nitrogen and carbon atoms to which they are attached, form a heterocyclic ring the heterocyclic ring contains at least two heteroatoms.

In the compound of general formula I, the groups R¹ and R² may be the same or different, but are preferably different. When any one or more of R, R¹ and R² is a substituted hydrocarbyl group, the substituent group is, or contains, at least one halogen atom such as fluorine, chlorine or bromine or contains at least one hetero atom selected from nitrogen, oxygen or sulphur as in the groups hydrocarbonoxy, hydrocarbonthio, acyl (that is hydrocarboncarbonyl), ester (that is acyloxy), hydrocarbonoxycarbonyl, or a nitrile group.

Each of the groups R, R¹ and R² and R³ independently may contain up to 25 carbon atoms but preferably contain up to 20 carbon atoms and especially not more than 10 carbon atoms. Each of the groups R, R¹, R² and R³ independently is preferably alkyl, cycloalkyl, aryl, aralkyl or alkaryl, especially containing up to 10 carbon atoms. If any of the groups R, R¹ or R² is substituted, the substituent or each substituent may be as previously described herein or, alternatively, the substituent may be a heteroatom in a heterocyclic group, which may itself be substituted with substituents as hereinbefore described. Heterocyclic groups include pyridyl, thienyl, imidazolyl, and thiazolyl. If any one of the groups R, R¹, R² R³ and is an alkyl group, this is preferably $C_{1-6}$-alkyl and more preferably $C_{1-5}$-alkyl. If any of the groups R, R¹, R² or R³ is a cyclic, including heterocyclic, group, the cyclic portion preferably contains at least five atoms such as in cyclopentyl, furyl or pyrrolyl groups, and more preferably at least six atoms, such as in cyclohexyl, phenyl, benzyl, pyridyl or naphthyl groups.

The group R is preferably hydrogen, an acyl group, especially one in which the hydrocarbon group attached to the carbonyl group contains not more than six carbon atoms much as benzoyl and acetyl, or an alkoxycarbonyl group, i.e. —COOR³ such as ethoxycarbonyl in which R³ is preferably alkyl especially $C_{1-6}$-alkyl, such as ethyl. When R is substituted, the substituent may be a group derived from a compound of formula I by the removal the group R so that the compound comprises two such groups linked through the group R. The group R¹ is preferably an alkyl group, especially $C_{1-6}$-alkyl such as methyl, ethyl, n-propyl or i-propyl or is a cyclic group such as phenyl.

The group R² is preferably $C_{1-6}$-alkyl such as a methyl group and it is especially preferred that R² is not an aralkyl group, particularly one in which there is only one carbon atom between the aryl group and the nitrogen atom.

Preferred compounds of formula I which can be used in the personal care formulations of the present invention are those in which the groups R¹ and R² together with the nitrogen and carbon atoms to which they are attached form a heterocyclic ring and, in particular, is a compound of the general formula (II):

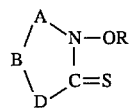

or a complex or salt thereof,
wherein:
R is as hereinbefore defined;
A and B are independently selected from —C(R⁴)₂—, —CR⁴=,

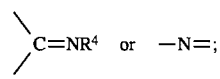

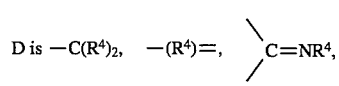

—NR⁴— or sulphur; and

R⁴ is hydrogen, hydrocarbyl, substituted hydrocarbyl or two groups R⁴ together with the carbon atom or carbon atoms to which they are attached form a 5- or 6-membered ring system, and any substituent on a hydrocarbyl group or acyl group is hydrocarbonoxy, hydrocarbonthio, acyl, acyloxy, hydrocarbonoxycarbonyl, a halogen atom or a nitrile group or may contain a further ring system of formula II.

Each of the groups $R^4$ may contain up to 25 carbon atoms, but preferably contains up to 20 carbon atoms and especially not more than 10 carbon atoms. It is preferred that $R^4$ is hydrogen or alkyl and especially $C_{1-6}$-alkyl or phenyl.

When $R^4$ is phenyl it may be substituted by one or more halogen atoms, especially chlorine, for example, 4-chlorophenyl.

In the compounds of formula II it is preferred that the heterocyclic ring contains at least two heteroatoms.

The groups, A, B and D can form part of a further ring system but generally not more than two of the groups A, B and D form part of a further ring system. The further ring system is typically a hydrocarbon ring system containing five or six carbon atoms, for example a cyclopentene, cyclohexane, cyclohexene, cyclohexadiene or benzene ring. The further ring system, if present, preferably contains one or both of the groups A and B. If only the group A forms part of a ring system, this may be a cyclohexane ring of the type

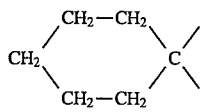

where the group A is the carbon atom with the two free valencies, which are linked to the group —NOR— and B respectively. If both A and B form part of a ring system, the further ring is then fused to the azolethione ring system; for example as in 3-hydroxy-4,5,6,7-tetrahydrobenzothiazol-2(3H)-thione.

In the preferred compounds used in the personal care formulations of the present invention, the groups A, B and/or D are not part of a further ring system. Thus, it is preferred that if A, B and/or D is a carbon atom, or substituted carbon atom, it is, inter alia, a group —CH=, —C(CH₃)=, —C(C₂H₅)=, —C(C₆H₅)=, —C(C₆H₄Cl)=,

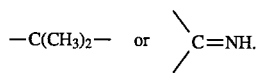

It will appreciated that in these groups the substituents on the ring carbon atoms, corresponding to $R^4$ in the definitions of A, B and D, are hydrogen, methyl, ethyl, phenyl, chlorophenyl, methyl and hydrogen, respectively.

Preferred compounds of formula (II), are those in which the ring atom in one of A, B and D is other than carbon. In these compounds D is preferably —N(R⁴)— or sulphur, especially sulphur.

In an especially preferred compound of the general formula (II), the groups A and B are both optionally substituted carbon atoms and the group D is a sulphur atom or optionally substituted nitrogen atom. Furthermore the groups A and B are preferably linked through a double bond, especially to form a group, —CH=CH—. It is especially preferred that D is a sulphur atom.

The anti-microbial agent is preferably a complex or salt of the compound of general formula (I) and especially a complex or salt of such a compound in which the group R is a hydrogen atom. The complex or salt can be with a non-metallic group such as an ammonium, quaternary ammonium or amine salt. Especially preferred is a metal complex or salt of the compound of general formula (II) in which the group R is a hydrogen atom.

The metal present in the salt or complex is a metal salt or complex of a metal of Groups IIIA to VA, IB to VIIB or VIII of the Periodic Table. All references herein to the Periodic Table are to the Periodic Table according to Mendeleeff, as set out on the inside rear cover of "Handbook of Chemistry and Physics" 49th Edition (1968–1969) published by The Chemical Rubber Co., Cleveland, Ohio, USA. In the metal complex or salt of the compound of the general formula (II), the metal may be a transition metal, for example a metal of group VIII, IB or IIB of the Periodic Table. Such metals include iron, copper and zinc, particularly such metals in their maximum possible valency state.

Preferred metal complexes or salts of the compound of formula (I) wherein $R^1$ and $R^2$ do not form a heterocyclic ring are those of the metals of Groups IIIA to VA or IB to VIIB with the exception of copper.

One or more metals may be present in the metal salt or complex of the compound of general formula I. However, it is generally preferred to use a complex or salt of only one metal.

Compound having useful properties are those in which the metal is a metal of Group IIB of the Periodic Table, for example zinc.

The metal salt or complex may contain ligands which give a neutral molecule, and the nature of these ligands will depend upon the particular method and conditions of preparation of the complex or salt. Thus, the metal salt or complex may contain ligands which include, for example, water, halides such as chloride, alcohols, ketones, carboxylic acids, amines, sulphoxides and the like. The ligand, if present, typically results from the reagents or solvents used to prepare the metal salt or complex and, in particular, the ligand results from the solvent used during the preparation of the metal salt or complex. The ligand may be a mixture of anionic groups and neutral ligands. In general the ligand, when present, is water.

Specific examples of the metal salts or complexes of the compounds formula I wherein $R^1$ and $R^2$ do not form a heterocyclic ring are the 2:1 complexes of N-methyl-N-hydroxythiobenzamide and zinc;

N-methyl-N-hydroxythioacetamide and zinc;

N-methyl-N-hydroxythiopropionamide and zinc;

N-methyl-N-hydroxythioisobutyramide and zinc or

N-methyl-N-hydroxythiobutyramide and zinc; and the 1:1 complex of N-methyl-N-hydroxythiobenzamide and silver.

Specific examples of the compounds of formula II including the metal salts or complexes thereof, are 3-hydroxy-4-methylthiazol-2(3H)-thione;

3-benzoyloxy-4-methylthiazol-2(3H)-thione;

3-hydroxy-4-phenylthiazol-2(3H)-thione;

3-hydroxy-4,5,6,7-tetrahydrobenzothiazol-2(3H)-thione;

3-acetoxy-4-methylthiazol-2(3H)-thione;

the glutaryl bis-ester of
3-hydroxy-4-methylthiazol-2(3H)-thione;

3-ethoxycarbonyloxy-4-methylthiazol-2(3H)-thione;

4,5-dimethyl-3-hydroxythiazol-2(3H)-thione;

4,5-dimethyl-3-acetoxythiazol-2(3H)-thione;

4-ethyl-3-hydroxy-5-methylthiazol-2(3H)-thione;

5,5-dimethyl-1-hydroxy-4-imino-3-
phenylimidazolidine-2-thione;

1-hydroxy-4-imino-3-phenyl-2-thiono-1,3-
diazaspiro[4.5]decane;

1-hydroxy-5-methyl-4-phenylimidazoline-2-thione;

4-ethyl-3-acetoxy-5-methylthiazol-2(3H)-thione;

4-(4-chlorophenyl)-3-hydroxythiazol-2(3H)-thione;

3-hydroxy-5-methyl-4-phenylthiazol-2(3H)-thione;

3-acetoxy-4-phenylthiazol-2(3H)-thione;

1-acetoxy-2-pyrrolindinethione;

1-acetoxy-5,5-dimethyl-2-pyrrolidinethione and 2-hydroxy-2,3-dihydro-1H-isoindol-1-thione.

Preferred compounds of the formula (I) have good anti-microbial activity together with low toxicity and are hence particularly useful for inclusion in personal care formulations.

Compounds of the general formula (I), and the salts and complexes thereof, are described, inter alia, in published European Patent Applications Numbers 249328, 392648 and 409617. Some compounds of the general formula (I) can be obtained by generally known procedures or, alternatively, such compounds, and the salts and complexes thereof, can be obtained by procedures disclosed in European Patent Applications Numbers 249328, 392648 and 409617, the disclosures of which are incorporated herein by reference.

The personal care formulation of the present invention may be any formulation which is capable of being used in any personal care application such as those previously described herein.

The anti-microbial agent may be incorporated into the personal care formulation using any suitable technique. Thus, the anti-microbial agent may be added to the personal care formulation as a solution, emulsion or dispersion in a suitable liquid medium. Alternatively the anti-microbial agent may be added, undiluted, to the personal care formulation or may be added with a solid carrier or diluent. The anti-microbial agent may be added to the pre-formed personal care formulation or may be added during the formation of the personal care formulation. If added during the formulation of the personal care formulation, the anti-microbial agent may be added separately or may be premixed with one of the components of the formulation.

The personal care formulation typically contains several components and these may be mixed in sequence or simultaneously using any mixing technique which is suitable for the particular formulation and such procedures are well known to the skilled worker. Typically the personal care formulation is a liquid or cream and can be obtained by stirring together the various components thereof, at an elevated temperature if desired.

The compound of the general formula (I), or the salt or complex thereof, may be the only anti-microbial agent present in the personal care formulation of the present invention or at least one further compound having anti-microbial characteristics may also be present. The use of a mixture of anti-microbial compounds can provide a formulation having a broader anti-microbial spectrum and hence one which is more generally effective than the components thereof. The further compound is typically a known anti-microbial agent and may be one possessing anti-bacterial, anti-fungal, anti-algal or other anti-microbial characteristics. If the formulation of the present invention contains a mixture of the compound of general formula (I), or salt or complex thereof, with other anti-microbial compounds, it typically contains from 1 to 99% by weight, relative to the weight of total anti-microbially active compounds, of the compound of general formula (I), or salt or complex thereof.

As examples of known antimicrobial compounds which may be used in combination with the compound of the general formula (I) there may be mentioned quaternary ammonium compounds such as diethyldodecylbenzyl ammonium chloride; dimethytoctadecyl(dimethylbenzyl)ammonium chloride; dimethyldidecylammonium chloride; dimethyldidodecylammonium chloride; trimethyl-tetradecylammonium chloride; benzyldimethyl($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecytbenzyltrimethylammonium chloride; benzyldimethyl($C_{12}$–$C_{18}$ alkyl)ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivates such as 1,3-bis(hydroxymethyl)-5,5-dimethylhydantoin; bis(hydroxymethyl)urea; tetrakis(hydroxymethyl)acetylene diurea; 1-(hydroxymethyl)-5,5-dimethylhydantoin and imidazolidinyl urea; amino compounds such as 1,3-bis(2-ethylhexyl)-5-methyl-5-aminohexahydropyrimidine; hexamethylene tetra amine; 1,3-bis(4-aminophenoxy)propane; and 2-[(hydroxymethyl)-amino]ethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2-bromo-2-bromomethylglutaronitrile, 2-chloro-2-chloromethylglutaronitrile, 2,4,5,6-tetra-chloroisophthalodinitrile; thiocyanate derivatives such as methylene bis thiocyanate; tin compounds or complexes such as tributyltin-oxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiozolin-3-one, 2-methylisothiazolin-3-one, 5-chloro-2-methyl-isothiazolin-3-one, 2-octylisothiazolin-3-one, 4,5-dichloro-2-octylisothiazolin-3-one, benzisothiazolin-3-one and 2-methylbenzisothiazolin-3-one; thiazole derivatives such as 2-(thiocyanomethylthio)-benzthiazole; and mercaptobenzthiazole; nitro compounds such as tris(hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as glutaraldehyde (pentanedial), p-chlorophenyl-3-iodopropargyl formaldehyde, and glyoxal; amides such as chloracetamide; N,N-bis(hydroxymethyl)chloracetamide; N-hydroxymethyl-chloracetamide and dithio-2,2-bis(benzmethyl amide); guanidine derivatives such as poly hexamethylene biguanide and 1,6-hexamethylene-bis[5-(4-chlorophenyl)biguanide]; thiones such as 3,5-dimethyltetrahydro-1,3,5-2H-thiadiazine-2-thione; triazine derivatives such as hexahydrotriazine and 1,3,5-tri-(hydroxyethyl)-1,3,5hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichlorophenoxy)phenol; thio-bis(4-chlorophenol) and 2-phenylphenol; sulphone derivatives such as diiodomethyl-paratolyl sulphone, 2,3,5,6-tetrachloro-4-(methylsulphonyl)pyridine and hexachlorodimethyl sulphone.

Although the use of a mixture of anti-microbial agents falls within the present invention, it is generally preferred to use only anti-microbial agents which are compounds of the general formula (I) or salts or complexes thereof and it will be appreciated that a mixture of such compounds may be used. Any further compounds having anti-microbial characteristics which are used are preferably compounds which have a combination of satisfactory anti-microbial activity and few, if any, undesirable side effects. It will be appreciated that not all compounds having anti-microbial characteristics are suitable for use in personal care formulations and that although suitable for use in combination with compounds of the general formula (I) or salts or complexes thereof such compounds, for example methylene bis-isocyanate and organic tin compounds, should generally not be present in the personal care formulations of the present invention.

The personal care formulation preferably contains not more than 0.25% w/v of anti-microbial agent or mixture thereof. It is particularly preferred that the personal care formulation contains less than 0.1%, and especially not more than 0.05% w/v of anti-microbial agent or mixture thereof. The proportion of anti-microbial agent which is present in the personal care formulation is dependent, at least partially, on the nature of the personal care formulation and the particular micro-organisms against which the formulation is particularly susceptible. Adequate protection may be achieved when the formulation contains less than 0.01%, or even less than 0.001% w/v of the anti-microbial agent. In general it is desirable that the personal care formulation contains at least 0.0001% w/v and especially at least 0.0005% w/v, of the compound of general formula (I) or a complex or salt thereof.

Further aspects of the present invention are described in the following illustrative examples. Unless otherwise stated all refer to parts by weight. Also, personal care formulations in accordance with the present invention were subjected to evaluation of the antimicrobial properties of the composition. The anti-microbial evaluation was effected, under aseptic conditions throughout, in the following manner.

In the anti-microbial evaluation, the formulations were tested for anti-microbial activity against bacteria and/or fungi. The bacteria used were either *Pseudomonas aeruginosa* or Staphylococcus *aureus*. The fungus used was *Candida albicans*.

Examples 1 and 2

A protein-containing shampoo was prepared having the following composition:

|  |  | Parts |
|---|---|---|
| Part A | SCI | 5 |
|  | Water | 68.9 |
| Part B | HM 935 | 10 |
|  | L7 | 5 |
|  | G-72200 | 2.8 |
|  | G 1823 | 6.0 |
|  | JR 400 | 0.05 |
|  | Crotein A | 2.0 |
|  | Sodium chloride | 0.25 |

SCI is Arlatone SCI a sodium cocoyl isethionate available from Imperial Chemical Industries PLC.
HM 935 is Tensuccin HM 935, a disodium alkyl ethoxy sulphosuccinate available from Imperial Chemical Industries PLC.
L7 is Tebobetain L7, a betain available from Th. Goldschmidt.
G-72200 is Atlas G-72200, an alkyl sulphonate available from Imperial Chemical Industries PLC.
G 1823 is Atlas G 1823, a blend of nonionic surfactants available from Imperial Chemical Industries PLC.
JR 400 is Polymer JR400, a water-soluble cationic cellulose ether available from Union Carbide Corporation.
Crotein A is a hydrolysed protein having an average molecular weight of 4000, available from Croda.

Part A of the composition was prepared by heating the components together, with stirring, to a temperature of 75° C. and continuing to stir at 75° C. until the Arlatone SCI had dissolved. The components forming Part B were pre-mixed by adding the components to a mixing vessel, in the order set out, and mixing by stirring at ambient temperature. Part A was added, whilst still at 75° C., to the Part B mixture and the mixture was stirred and allowed to cool to ambient temperature (about 20° C.).

To aliquots (20 parts) of the shampoo formulation prepared as described were added various anti-microbial agents at concentrations of 125, 62.5, 31.25, 7.8 and 1.56 ppm of active ingredient, not all of the anti-microbial agents being used at all of these levels. The anti-microbial agents, and the levels used are as set out in Table One.

One sample of a mixture of the shampoo formulation and the anti-microbial agent was stored for one month (4 weeks) at 40° C. and a duplicate sample of the mixture was stored for one month at ambient temperature (about 20° C.).

The variants thus obtained were then challenged with a 0.2 parts by volume inoculum of a 24 hour culture of *Pseudomonas aeruginosa* (ATCC 19429) containing approximately $1 \times 10^8$ colony forming units (cfu's) per $cm^3$. The variants were than incubated in the dark at 25° C., and samples (one $cm^3$) were taken after 24 hours, 48 hours and 7 days. The number of surviving bacteria was determined by the decimal dilution method and the viable cells enumerated by incubation of the survivor detection plates at 30° C. for three days.

The results are shown in Table One in which the concentration of anti-microbial agent is the minimum required to reduce the count of viable cells to less than $10^2$ cells $cm^{-3}$.

After removing the seven day sample, the samples of the shampoo formulation were challenged with a further 0.2 parts of a similar *Pseudomonas aeruginosa* culture and incubation at 25° C. was continued. Further one $cm^3$ samples were removed after 24 hours, 48 hours and 7 days and the number of surviving bacteria was determined in the same manner.

The results of the second challenge are also set out in Table One.

TABLE ONE

| Ex or Comp Ex | AMA (a) | MLC (b) Challenge 1 | | | Challenge 2 | | |
|---|---|---|---|---|---|---|---|
| | | 24h | 48h | 7d | 24h | 48h | 7d |
| A | BL | 31.25 | 1.56 | 1.56 | 1.56 | 1.56 | 1.56 |
| B | BX | 31.25 | 31.25 | 31.25 | 31.25 | 31.25 | 31.25 |
| C | 115 | 7.8 | 31.25 | 31.25 | 62.5 | 31.25 | 31.25 |
| D | 200 | 7.8 | 7.8 | 7.8 | 62.5 | 62.5 | 62.5 |
| E | CG | 1.56 | 1.56 | 1.56 | 7.8 | 1.56 | 1.56 |
| 1 | ZTA | GT125 | 7.8 | 7.8 | 31.25 | 31.25 | 31.25 |
| F | C | 8.0E3 | 7.0E4 | 2.0E6 | 2.8E8 | GT3.0E8 | 4.0E6 |
| G | BL(S) | 125 | 1.56 | 1.56 | GT125 | 62.5 | 62.5 |
| H | BX(S) | 62.5 | 1.56 | 1.56 | 62.5 | 62.5 | 62.5 |
| I | 115 | GT62.5 | 31.25 | 1.56 | GT62.5 | GT62.5 | GT62.5 |
| J | 200(S) | GT62.5 | 31.25 | 1.56 | GT62.5 | GT62.5 | GT62.5 |
| K | CG(S) | 1.56 | 1.56 | 1.56 | 1.56 | 1.56 | 1.56 |
| 2 | ZTA(S) | GT125 | 62.5 | 62.5 | GT125 | 62.5 | 62.5 |
| L | C(S) | 2.5E3 | 3.0E3 | 5.2E4 | 6.0E5 | 4.0E5 | 3.8E5 |

Notes to Table One
(a) AMA is anti-microbial agent
BL is a commercially available anti-microbial agent containing, as the active ingredient 2-bromo-1,3-dihydroxy-2-nitropropane.
BX is a commercially available anti-microbial agent containing, as the active ingredient, 5-bromo-5-nitro-1,3-dioxane.
115 is a commercially available anti-microbial agent containing, as the active ingredient, imidazolidinyl urea.
200 is a commercially available anti-microbial agent containing, as the active ingredient, an isomer of 1-(3-chloroallyl)-3,5,7-triaza-1-azoniadamantane chloride.
CG is a commercially available biocide containing a mixture of 5-chloro-2-methyl-4-isothiazolin-3-one and 2-methyl-4-isothiazolin-3-one as the active ingredient.
ZTA is the 2:1 complex of 3-hydroxy-4-methyl-thiazol-2(3H) thione and zinc.
C is the control with no added anti-microbial agent
(S) indicates the samples has been itored for one month at 40° C. The other samples were stored for one month at ambient temperature.
(b) MLC is the minimum concentration (in ppm w/v) of the anti-microbial agent required to reduce the viable cell count to less than $10^2$ cells $cm^{-3}$
24h is sample taken after 24 hours incubation
48h is sample taken after 48 hours incubation
7d is sample taken after 7 days incubation
GT means greater than
The figures opposite C and C(S) represent the cell count, wherein E indicates the logarithmic power of 10, that is 8.0E3 means $8.0 \times 10^3$.

Example 3

An oil in water emulsion of a type typically used as a base cream was prepared having the following composition:

| | | Parts |
|---|---|---|
| Part A | PEG(5)SS | 4.0 |
| | PEG(21)SA | 2.0 |
| | Paraffin oil | 9.0 |
| | 812 | 5.0 |
| | S3 | 2.0 |
| Part B | Propyleneglycol | 1.0 |
| | PEGS | 1.0 |
| | Demineralised water | 76.0 |

PEG(5)SS is poly(oxyethylene)octadecyl octadecanoate containing an average of five oxyethylene units.
PEG(21)SA is poly(oxyethylene)octadecanol containing an average of 21 oxyethylene units.
812 is a triglyceride of fractionated coconut fatty acids containing predominantly from 8 to 10 carbon atoms.
S3 is a mixture of 70 parts of poly(oxypropylene)octadecanol containing an average of 15 oxypropylene units with 30 parts cyclic tetra(dimethylsiloxane)
PEGS is an ethoxylated sorbitol comprising predominantly mono-ethoxylated-sorbitol.

Part A and Part B of the composition were prepared separately by stirring together the components thereof and heating up to 75° C. Part A was added to Part B at 75° C. whilst stirring thoroughly and stirring was continued until the mixture was well homogenised. The mixture was then allowed to cool to ambient temperature whilst continuing to stir thoroughly.

To aliquots (20 parts) of the emulsion were added various anti-microbial agents at concentrations of 500, 125, 31.25 and 7.8 ppm of active ingredients.

One sample of each mixture was inoculated with 0.2 parts by volume of a 24 hour culture of Staphylococcus aureus (ATCC 6538) containing $10^8$ cells $cm^{-3}$. Duplicate samples of each mixture were inoculated with 0.2 parts by volume of a 48 hour culture of Candida albicans (ATCC 10231) containing $10^8$ cells $cm^{-3}$.

The samples were then incubated and samples removed after 24 hours, 48 hours and 7 days as described in Examples 1 and 2 with the exception that the samples were not subjected to a further challenge after seven days.

The results obtained are set out in Table Two.

TABLE TWO

| Ex or Comp Ex (c) | AMA (a) | MLC (b) SA(d) 24h | 48h | 7d | CA(e) 24h | 48h | 7d |
|---|---|---|---|---|---|---|---|
| 3 | ZTA | 500 | 31.25 | 7.8 | 31.25 | 31.25 | 31.25 |
| M | SP | GT500 | 500 | 125 | 500 | 500 | 31.25 |
| N | ZP | GT500 | GT500 | 500 | 500 | 500 | 31.25 |
| O | C | 2.0E8 | 4.6E7 | 2.5E8 | 1.0E7 | 1.3E7 | 2.0E6 |

Notes to Table Two
(a) and (b) are both as defined in Notes to Table One.
(c) SP is the sodium salt of 1-hydroxy-2-pyridinethione
ZP is the 1:2 complex of zinc with 1-hydroxy-2-pyridinethione
(d) SA are the results obtained in the challenge test using *Staphylococcus aureus*.
(e) CA are the results obtained in the challenge tests using *Candida albicans*.

Examples 4–14

A shampoo having the following composition

| Empicol* ESB70 | 16.5 parts |
|---|---|
| Empilan* 2502 | 2.0 parts |
| Empigen* BB | 5.0 parts |
| Sodium chloride | 1.0 part |
| Citric Acid | to pH 7 |
| Water | to 100 parts |

*Empicol, Empilan and Empigen are registered Trademarks of Albright and Wilson, was prepared by stirring the Empicol ESB70 in water, and then adding the Empilan 2502 followed by the Empigen BB to give a clear homogenous solution. An aqueous solution of citric acid was added with stirring to give a pH of 7. Finally, the sodium chloride was added and the whole diluted to 100 parts by adding water.

Aliquots (4 parts) of the above shampoo were then prepared with concentrations of the biocides indicated in Table 3 at 500 and 125 ppm of active ingredient.

The above samples were then challenged with a 0.2 parts by volume inoculum of a 24 hour culture of *Pseudomonas aeruginosa* (ATCC 19429) containing approximately $1 \times 10^8$ colony forming units (cfu's) per milliliter. The samples were then incubated in the dark at 25° C., 1 milliliter samples taken after 24 hours, 48 hours and 7 days and the number of surviving bacteria determined.

The results are shown in Table 3.

TABLE 3

| Example | Conc (ppm) | Viable bacteria after 24 hr | 48 hr | 7 days |
|---|---|---|---|---|
| 4 | 500 | 1.2E4 | GT3.0 E4 | GT3.0 E4 |
|   | 125 | 1.7E4 | GT3.0 E4 | GT3.0 E4 |
| 5 | 500 | 7.6E3 | LT 10 | LT 10 |
|   | 125 | 6.2E3 | LT 10 | LT 10 |
| 6 | 500 | 1.4E4 | GT3.0 E4 | LT3.0 E4 |
|   | 125 | 4.5E4 | GT1.0 E4 | LT3.0 E4 |
| 7 | 500 | 3.5E4 | GT3.0 E4 | GT3.0 E4 |
|   | 125 | 2.4E4 | GT3.0 E4 | GT3.0 E4 |
| 8 | 500 | 1.2E3 | LT 10 | LT 10 |
|   | 125 | 2.1E3 | LT 10 | LT 10 |
| 9 | 500 | 2.0E3 | 1.7 E2 | LT 10 |
|   | 125 | 2.6E3 | 8.0 | LT 10 |
| 10 | 500 | 1.8E4 | GT3.0 E4 | 2.2 E5 |
|   | 125 | 2.1E4 | GT3.0 E4 | GT3.0 E4 |
| 11 | 500 | LT 10 | LT 10 | LT 10 |
|   | 125 | 9.1E2 | LT 10 | LT 10 |
| 12 | 500 | 1.3E3 | LT 10 | LT 10 |
|   | 125 | 1.5E4 | GT3.0 E4 | 8.3 E5 |
| 13 | 500 | 5.2E2 | LT 10 | LT 10 |
|   | 125 | 2.1E3 | LT 10 | LT 10 |

TABLE 3-continued

| Example | Conc (ppm) | Viable bacteria after 24 hr | 48 hr | 7 days |
|---|---|---|---|---|
| 14 | 500 | 4.4E3 | LT 10 | LT 10 |
|   | 125 | 3.3E3 | LT 10 | LT 10 |
| Control |   | 6.2E5 | 6.1E6 | 2.3E6 |

Notes to Table 3
LT = less than
GT = Greater than
E = logarithmic power of 10
Empicol ESB70 is a 60% aqueous solution of sodium laurylethoxysulphate
Empilan BBB70 is coconut diethanoiamide
Empigen BB is an aqueous 30% sulotion of an alkyl ($C_{12}/C_{14}$) betaine
Example 4 is 3-hydroxy-4-methylthiazol-2(3H)-thione
Example 5 is the 2:1 zinc complex of Example 4
Example 6 is the 3:1 yttrium complex of Example 4
Example 7 is the 2:1 manganese complex of Example 4
Example 8 is the 3:1 cobalt complex of Example 4
Example 9 is the 3:1 scandium complex of Example 4
Example 10 is the 2:1 molybdenyl complex of Example 4
Example 11 is the 3:1 indium complex of Example 4
Example 12 is the 2:1 vanadyl complex of Example 4
Example 13 is the 2:1 cobalt complex of Example 4
Example 14 is the 2:1 zinc complex of Example 4

Example 15

The procedure of Examples 4–14 were repeated using the 1:1 silver complex of N-methyl-N-hydroxythiobenzamide at four different concentrations. The results are displayed in Table 4.

TABLE 4

| Example | Conc (ppm) | Viable bacteria after 24 hrs | 48 hrs | 7 days |
|---|---|---|---|---|
| 15 | 500 | LT 10 | LT 10 | LT 10 |
|   | 125 | LT 10 | LT 10 | LT 10 |
|   | 31.25 | LT 10 | LT 10 | LT 10 |
|   | 7.13 | LT 10 | LT 10 | LT 10 |
| Control |   | 2.7 E8 | 7.8 E7 | 8.3 E7 |

Notes to Table 4
LT = less than
E = logarithmic power of 10

We claim:

1. A personal care formulation which contains a) an antimicrobial agent of formula (I)

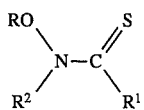

(I)

or a metal complex or salt thereof;
wherein

R is hydrogen, $C_{1-6}$-hydrocarbon carbonyl or —$COOR^3$;

$R^1$ is $C_{1-10}$-alkyl or phenyl;

$R^2$ is $C_{1-10}$-alkyl;

$R^3$ is $C_{1-6}$-alkyl; or $R^1$ and $R^2$ together with the carbon and nitrogen atoms to which they are attached form a heterocyclic ring and the compound of formula I is a compound of formula II

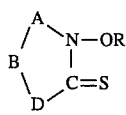

(II)

wherein

A and B are independently selected from the group consisting of —$C(R^4)_2$—, —$CR^4$=, >C=$NR^4$ and —N=;

D is selected from the group consisting of —$C(R^4)_2$—, —$CR^4$=, >C=$NR^4$, —$NR^4$— and sulphur;

$R^4$ is hydrogen, $C_{1-6}$-alkyl, phenyl or phenyl substituted by halogen; or

A forms part of a cyclohexane ring or two of the groups A, B and D form part of a cyclohexane, cyclohexene or benzene ring; and b) a component selected from the group consisting of a hand lotion, foundation cream, emollient cream, facial washing cream, shaving cream, after-shave lotion, sunscreen lotion, sunscreen cream, after sun lotion, antiperspirant, deodorant, hair gel, hair mousse, mascara, eye shadow, eyeliner, lipstick, lip gloss, facial blush, rouge, foundation, fragrance, shampoo, shampoo gel, conditioning rinse, foam bath liquid, miscible bath oil or soluble bath oil and liquid soap.

2. A formulation as claimed in claim 1 wherein $R^1$ is a $C_{1-6}$ lower alkyl group.

3. A formulation as claimed claim 1 wherein each of $R^2$ and $R^3$ is independently a $C_{1-6}$ lower alkyl group.

4. A formulation as claimed in claim 1 wherein D is a sulphur atom.

5. A formulation as claimed in claim 1 wherein the anti-microbial agent is a metal complex or salt.

6. A formulation as claimed in claim 5 wherein the metal is from Groups IIIA to VA, IB to VIIB and VIII of the Periodic Table.

7. A formulation as claimed in claim 1 wherein the anti-microbial agent is a zinc complex or salt.

8. A formulation as claimed in claim 1 which contains an antimicrobial agent selected from the group consisting of the 2:1 complexes of zinc N-methyl-N-hydroxythiobenzamide;

zinc N-methyl-N-hydroxythioacetamide;

zinc N-methyl-N-hydroxythiopropionamide;

zinc N-methyl-N-hydroxythioisobutyramide;

zinc N-methyl-N-hydroxythiobutyramide; and zinc 3-hydroxy-4-methylthiazol-2(3H)-thione.

9. A formulation as claimed in claim 1 which contains an antimicrobial agent selected from the group consisting of 3-hydroxy-4-methylthiazol-2(3H)-thione 3-benzoyloxy-4-methylthiazol-2(3H)-thione;

3-hydroxy-4-phenylthiazol-2(3H)-thione;

3-hydroxy-4,5,6,7-tetrahydrobenzothiazol-2(3H)-thione;

3-acetoxy-4-methylthiazol-2(3H)-thione;

4,5-dimethyl-3-hydroxythiazol-2(3H)-thione;

4,5-dimethyl-3-acetoxythiazol-2(3H)-thione;

4-ethyl-3-hydroxy-5-methylthiazol-2(3H)-thione;

5,5-dimethyl-1-hydroxy-4-imino-3-phenylimidazoline-2-thione;

1-hydroxy-4-imino-3-phenyl-2-thiono-1,3-diazaspiro[4,5]decane;

1-hydroxy-5-methyl-4-phenylimidazoline-2-thione;

4-ethyl-3-acetoxy-5-methylthiazol-2(3H)-thione;

4-(4-chlorophenyl)-3-hydroxythiazol-2(3H)-thione;

3-hydroxy-5-methyl-4-phenylthiazol-2(3H)-thione;

3-acetoxy-4-phenylthiazol-2(3H)-thione;

1-acetoxy-2-pyrrolindinethione;

1-acetoxy-5,5-dimethyl-2-pyrrolidinethione;

2-hydroxy-2,3-dihydro-1H-isoindol-1-thione and the salts or complexes thereof.

10. A formulation as claimed claim 1 which contains not more than 0.25% w/v of anti-microbial agent.

* * * * *